United States Patent [19]

Rokach et al.

[11] 4,292,430
[45] Sep. 29, 1981

[54] 2,3-SUBSTITUTED-1,2-ISOTHIAZOLIUM SALT ANTIMICROBIALS

[75] Inventors: Joshua Rokach, Chomedey-Laval, Canada; Clarence S. Rooney, Worcester; Edward J. Cragoe, Jr., Lansdale, both of Pa.

[73] Assignee: Merck & Co., Inc., Rahway, N.J.

[21] Appl. No.: 854,292

[22] Filed: Nov. 23, 1977

[51] Int. Cl.³ .......................................... C07D 275/02
[52] U.S. Cl. .................................... 548/206; 548/214; 424/270
[58] Field of Search .................. 260/302 A; 548/206, 548/214, 212

[56] References Cited

U.S. PATENT DOCUMENTS 3,155,678  11/1964  Hatchard .................... 260/302

FOREIGN PATENT DOCUMENTS 2012336  3/1970  France .................... 260/302 A

OTHER PUBLICATIONS

Lewis et al., "J. Het. Chem.", vol. 8, p. 571 (1971).
Holland et al., "J. Chem. Soc.", p. 7277 (1965).

*Primary Examiner*—Nicholas S. Rizzo
*Attorney, Agent, or Firm*—Raymond M. Speer; Edmunde D. Riedl

[57] ABSTRACT

2,3-Substituted-1,2-isothiazolium salts have antibacterial and antifungal activity and are useful in agriculture against diseases and decay of fruits and vegetables, as well as a slimicide in industry.

3 Claims, No Drawings

2,3-SUBSTITUTED-1,2-ISOTHIAZOLIUM SALT ANTIMICROBIALS

This invention relates to a new class of antibacterial and antifungal compounds, particularly 2,3-substituted-1,2-isothiazolium. The 1,2-isothiazolium salts of this invention have the structural formula:

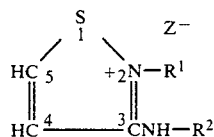

where $R^1$ is hydrogen or an alkyl group of from 1–16 carbon atoms, phenyl or benzyl; $R^2$ is an alkyl group of 1–16 carbon atoms, phenyl or benzyl; and $Z^-$ is a counter anion. In general, it is preferred that the alkyl group whether $R^1$ or $R^2$ contain from 1–4 carbon atoms. The term "alkyl" includes straight or branched hydrocarbon radicals such, for example, as methyl, ethyl, propyl, isopropyl, butyl, sec-butyl, t-butyl, pentyl, 1-(2-ethyl)propyl, hexyl, 1-(2,3-dimethyl)butyl, heptyl, 1-(2-ethyl-4-methyl)butyl, octyl, nonyl, decyl, dodecyl, hexadecyl, 4-t-butylphenyl, 2,4-diethylphenyl, 4-ocylphenyl, 3-heptylphenyl, 4-hexylphenyl and 2,4,6-triethylphenyl.

The compounds of this invention are prepared according to the following reaction sequence.

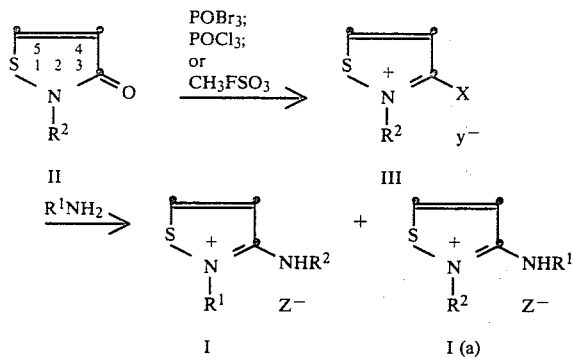

where X is chloro, bromo or methoxy, $y^-$ is $FSO_3$ or Br, Cl, and $Z^-$ is a counter ion. Where $R^1$ and $R^2$ differ, various ratios of isomers I and I (a) are produced which can be separated by standard means.

The starting material, the 2-substituted-1,2-isothiazole-3-ones of formula II is available by means known in the prior art. After obtaining the appropriate 1,2-isothiazole-3-one, the 2-substituted-3-chloro or 3-methoxy-1,2-isothiazoles of formula III are prepared by the following methods.

Those compounds of formula II where X is chloro or bromo are prepared by admixing the isothiazole-3-one with at least a molar equivalent of phosphorous trichloride or phosphorous tribromide. For the best yield it is preferred the minimum amount of the phosphorous trihalide be used. The reaction mixture is then warmed slightly to 25° C. to 30° C. for 1–6 hours. Then an excess of diethylether can be added to effect separation of intermediate III as a gum.

When Intermediate III is prepared where X is methoxy, the 1,2-isothiazole-3-one is admixed with a 1 to 2 molar excess of methylfluorosulfonate neat or in an inert solvent such as dichloromethane. The reaction mixture is then gently heated to 20° C. to for about few minutes to several hours.

To compound III preferably in situ is then added the amine $R^1NH_2$. It is much preferred to employ compounds of formula III where X is chloro or bromo rather than methoxy. The reaction can be carried out in acetonitrile solvent. When X is Cl or Br two molar equivalents of the primary amine are employed. Where X is methoxy only one molar equivalent of the primary amine is necessary. The reaction is usually carried out at temperatures from 0° C. to 25° C.

Examples of suitable amines include ammonia; methyl amine; 1-ethyl amine; 1-isopropyl amine; 2-isopropyl amine; 3-butyl amine; 4-pentyl amine; 7-heptyl amine; aniline; benzyl amine; 1-octyl amine; 1-laural amine; 4-octyl amine; 1-(2-chloroethyl)amine and the like.

Suitable anions $Z^-$ for the 1,2-isothiazolium salt I include halide, e.g., chloride, bromide or iodide or sulfate bisulfate, fluorosulfonate, nitrate, phosphate, acetate, propionate, maleate, succinate, laurate, oleate, palmitate, stearate, ascorbate, gluconate, citrate, carbonate, bicarbonate, benzoate, salicylate, pamoate, phthalate, furoate, picolinate, dodecylbenzenesulfonate, laurylethersulfate, nicotinate and the like. Generally, when the salt anion $Z^-$ is fluorosulfonate or chloride, it can be replaced with another suitable anion by well known anion exchange techniques.

Compound I include $R^1$ is methyl or ethyl can also be prepared by the following scheme.

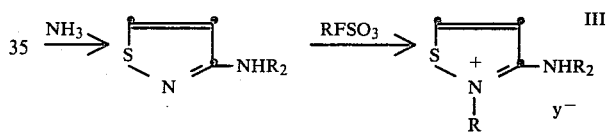

in which R is methyl or ethyl and $R_2$ and $y^-$ are as previously defined. The reaction is carried out by bubbling ammonia into a solution comprising compound III and optionally an inert solvent. After from ½ to 6 hours at from 0° C. to 25° C., the reaction is reasonably complete. Then, a 1–2 molar excess of methylfluorosulfonate and reacting as before stated.

The following examples are illustrative of the invention viewed as any limitation thereon.

EXAMPLE I

2-Methyl-3-chloroisothiazoliumfluorosulfonate

3-Chloroisothiazole (Chem. Bor., 96, 944 (1963) 10 g. (0.084 mole) was placed in a 250 ml. pressure bottle, cooled in ice water and methylfluorosulfonate (10 g., 0.088 mole) was added. The bottle was sealed and after several minutes a vigorous exothermic reaction occurred, the contents becoming solid. The reaction was cooled and the white solid was triturated with methylene chloride and filtered yielding 17.9 g. (92%) of the 2-methyl-3-chloroisothiazoliumfluorosulfonate.

EXAMPLE II

2-Methyl-3-methylaminoisothiazolium Chloride

2-Methyl-3-chloroisothiazoliumfluorosulfonate (5.67 g., 0.24 mole) was dissolved in acetonitrile (20 ml.) and a solution of methylene (1.51 g., 0.48 mole) in acetonitrile was added dropwise. Methylamine hydrochloride gradually crystallized from the reaction mixture. The reaction was stirred at room temperature for one hour, filtered and evaporated under reduced pressure. The residue was redissolved in acetonitrile (15 ml.), filtered again and evaporated. The residue (5.5 g.) crystallized on cooling. The fluorosulfonate salt was passed through excess Bio-Rad. AG1-X8 ion exchange resin (chloride form). The aqueous eluate was evaporated to give the crystalline salt, which was recrystallized from isopropanol ether; 3.2 g. was recovered. M.P. 205° C. (dec.).

EXAMPLE III

2-Ethyl-3-chloroisothiazoliumfluorosulfonate

Prepared in 95% yield as described in Example I from 3-chloroisothiazole and ethylfluorosulfonate.

EXAMPLE IV

2-Ethyl-3-ethylaminoisothiazolium Chloride

Prepared from 2-ethyl-3-chloroisothiazoliumfluorosulfonate and ethylamine as described in Example II, m.p. 136° C.–138° C.

EXAMPLE V

2-Methyl-3-aminoisothiazolium Chloride

Freshly distilled methylfluorosulfonate (11.5 g., 0.1 mole) was added to an ice-water cooled solution of 3-aminoisothiazole, J. Chem. Soc., 7277 (1965) (9 g., 0.09 mole) dissolved in methylene chloride (100 ml.). A vigorous reaction occurred and a precipitate formed. The reaction was brought to room temperature, stirred for one hour and stripped to a heavy oil, leaving a quantitative yield of the fluorosulfonate salt. The fluorosulfonate was exchanged for chloride as described in Example II. The resulting aqueous solution of the chloride salt was charcoaled and evaporated at low pressure. The residue was redissolved in a minimum volume of isopropanol and stored at 0° C. to 5° C. for four days. The cream-colored crystals (3.9 g.) were filtered. A second crop of 0.67 g. was recovered from mother liquors; yield 34%, m.p. 147° C.–151° C.

Analysis calculated for $C_5H_7N_2ClS$: C, 32.11; H, 4.04; N, 18.72; S, 21.43; Cl, 23.69. Found: C, 31.94; H, 4.50; N, 18.65; S, 21.27; Cl, 23.48.

EXAMPLE VI

2-Phenyl-3-chloroisothiazolium Chloride

2-Phenyl-4-isothiazolium-3-one (J. Het. Chem., 8, 571 (1971) (1 g.) is stirred at room temperature with phosphorous oxychloride (3–5 ml.); the progress of the reaction was monitored by TLC for disappearance of starting material. The reaction can be speeded up by warming to 60° C. Ether is added to precipitate a white gum. The residue was flushed once more with ether and decanted. The material is used as such in the next step.

EXAMPLE VII

3-Phenylaminoisothiazole

The 2-phenyl-3-chloroisothiazolium chloride prepared in the example is dissolved in 10 ml. acetonitrile and ammonia gas is bubbled through the reaction mixture for a few minutes. The reaction mixture is filtered and evaporated to dryness. The residue was partioned between chloroform and dilute base. The organic phase is dried over sodium sulfate and evaporated. Yield (95%). M.P. 156-8 (benzene).

EXAMPLE VIII

2-Methyl-3-phenylaminoisothiazoliumfluorosulfonate

3-Phenylaminoisothiazole was treated with methyl fluorosulfonate as per Example V to yield the 2-methyl-3-phenylaminoisothiazoliumfluorosulfonate in 72% yield. M.P. 170° C.–172° C. (acetonitrile, ether).

Analysis calculated for $C_{10}H_{11}FN_2O_3S_2$: C, 41.37; H, 3.82; F, 6.54; N, 9.65; S, 22.09. Found: C, 41.40; H, 4.30; F, 6.64; N, 9.79; S, 22.07.

As described above by appropriately adjusting the starting materials the following products can be obtained.

| $R^1$ | $R^2$ |
| --- | --- |
| Hydrogen | Methyl |
| Hydrogen | Propyl |
| Hydrogen | Isopropyl |
| Hydrogen | Phenyl |
| Hydrogen | Benzyl |
| Hydrogen | Lauryl |
| Methyl | Methyl |
| Methyl | Benzyl |
| Methyl | Phenyl |
| Methyl | Lauryl |
| Propyl | Propyl |
| Propyl | Isopropyl |
| Propyl | Benzyl |
| Propyl | Phenyl |
| Propyl | Lauryl |
| Benzyl | Methyl |
| Benzyl | Propyl |
| Benzyl | Isopropyl |
| Benzyl | Lauryl |
| Phenyl | Propyl |
| Phenyl | Isopropyl |
| Phenyl | Benzyl |
| Phenyl | Phenyl |
| Phenyl | Lauryl |
| Lauryl | Methyl |
| Lauryl | Propyl |
| Lauryl | Isopropyl |
| Lauryl | Benzyl |
| Lauryl | Lauryl |
| Isopropyl | Isopropyl |

The compounds of our invention are broad spectrum antibacterial and antifungal agents, For use, the compounds described herein can be applied neat or employed in a diluted form. Satisfactory diluents include any inert material not destructive of the antimicrobial activity and especially liquid formulations comprising aqueous dispersions, solutions, and emulsions. Solid diluents include talc, corn starch, alumina and diatomaceous earth. The antimicrobial agents of this invention can also be deposed on materials such as natural fibers including paper, cotton, wool and synthetic fibers such as nylon, polypropylene, as well as upon inanimate surfaces including hard surfaces such as wood, glass, metal, tile, rubber, plastic, and porous surfaces such as concrete leather and the like.

Another application is alone or in solution or suspension or in conjunction with soaps or detergents for use in cleansing the skin, particularly in presurgical scrubbing formulations, or in formulations for controlling the growth of *Corynebacterium acnes*. *C. acnes* is a strain of bacteria implicated in acne conditions, especially *Acne vulgaris*, wherein applications of as little as 1 to 5 ppm. is effective in controlling such skin dwelling bacteria. Larger concentrations can be used, if desired, without irritation or discomfort such as 2500 ppm and higher. Where the cleansing formulation is diluted with water upon use, the formulation can comprise from 0.01% by weight and more of the compounds of this invention.

In addition, the compounds described herein can be employed in impounded water, such as swimming pools, ponds or industrially-used water such as paper-mill water to inhibit growth of undesirable bacteria, fungi, and/or algae at levels as low as 0.5-5 ppm.

In the control of slime-producing microorganisms and algae in recirculating industrial waters, particularly cooling operations and especially installations such as cooling towers, the compounds of this invention are usually employed alone, but can also be used in combination with other antimicrobial agents. Concentrations in the recirculating water of as little as $1 \times 10^{-4}\%$ by weight are effective in inhibiting microbial growth. To insure effectiveness, especially against more resistant strains of microorganisms, and also when make-up water is added to replace water lost by evaporation and the like, concentrations of from $1 \times 10^{-4}\%$ to $5 \times 10^{-2}\%$ by weight are most satisfactory. Dosage may be continuous or as intermittent "shock treatment", i.e., addition in a 10-20 minute period every 4-8 hours. They are especially useful against bacteria and fungi responsible for stunting the growth and even destruction of many types of crop-producing plants. In agriculture, severe problems are faced in the raising of cotton, beans, corn and other crops because of the loss of yield per acre due to the action of soilborne fungi on seed and on the roots of the young plants. Control or elimination of these losses can be accomplished by the use of the compounds herein described as soil disinfectants in accordance with the invention. They can also be used for the control of bacterial and fungal diseases on trees and stored crops.

In formulating the compounds of this invention for the above uses, these compounds can be employed in combination with other antimicrobial agents, surfactants, insecticides, defoamers, odorants, or as chelates of metals such as copper, calcium, magnesium and iron.

Wettable powder formulations for use as a dispersant in water represent a practical means for good distribution in soil. Other methods of achieving the same results include the preparation of dusts. All of the thiazolium salts can be blended as fine powders with the commonly used powder diluents such as talc, clay, refined silicates, wood flour, sand, magnesium oxide, calcium carbonate, fuller's earth, kaolin, diatomaceous earth, mica, pumice and the like. The powder can have the following formulation:

|  | Percent |
| --- | --- |
| 2,3-Substituted-1,2-isothiazolium Salt | 1-75 |
| Inert Diluent (clay, talc, etc.) | 25-99 |

The mixtures may be finely powdered, e.g., to the 1-10 micron average particle size, or be made by blending the already finely powdered ingredients.

For application as agricultural disinfectants the dusts may be applied to the seed and surrounding soil at the time of planting. The concentration of the sterilant is adjusted to give an effective, nonphytotoxic dosage in the soil. In general, the soil concentration should be from 10 to 25 parts per million (of active ingredient). For most economical and effective use the dusts can be applied in bands of 6 to 8 inches centered on the rows just prior to seeding. The material can then be rototilled to a depth of several inches. This mode of treatment saves material and protects the root system of young plants against microbial attack. For the protection of a given crop, such as cabbage, the band spread of antimicrobial can vary from 8 inches for black root disease to 12-15 inches for club root disease prevention. Similarly, the depth to which the fungicide should be distributed can vary from 2 to 6 inches.

The wettable powders can be prepared by the addition of 0.1-5% of a wetting agent to the powder blends. Many dispersing agents are commercially available which are nonphytotoxic at the required concentrations. These may, for example, be alkali metal and amine salts of sulfated and sulfonated acids, alcohols, and oils, or polyethoxylated alkyl phenols, long chain fatty amine quaternary salts, partial phenols, long chain fatty amine quaternary salts, partial fatty acid esters of polyhydric alcohols, etc. Some dispersants can be used in preparing emulsifiable concentrates of the polyamines in organic solvents. Many of these agents are available in solvent-soluble form. The manner of application to the soil is similar to the dusts. Spray equipment is used to spread the suspensions or emulsions over the soil and by discing, the fungicidal agents can be uniformly distributed to varying depths. Spray application is also effective for band-limiting the dosages.

Other agricultural uses for these formulations involve the eradication of bacterial blights of plants by application to the involved surface areas. The compounds of this invention show high orders of bacterial inhibition and are especially useful for this purpose. Some of the diseases which are of commercial importance in decreasing yield and quality and are controlled by the compositions of the invention are fire blight of apple and pear, bacterial spot on stone fruit, cherry leaf spot, walnut blight, common blight of bean, bacterial spot of tomato and pepper, and potato seed piece decay. The effective concentration required varies from 5-200 parts per million parts of the material to be protected. They may be applied as dusts, powder dispersions in water as emulsions in water, or as aqueous dipping baths. Other plant diseases which can be controlled by treatment with these formulations are fungal in origin, such as the many kinds of powdery mildew and leaf scabs.

For seed treatment, proportions as low as 1 to 4 ounces per hundred weight (550 to 600 ppm on seed) are effective against various fungi.

The compounds of the invention can be used in form of aqueous suspensions or emulsions, the base products being generally insoluble in water. For this type of formulation various powdered carriers can be employed to aid in achieving uniform distribution. Talc, fuller's earth, calcium silicate, calcium carbonate, clays and the like are admixed with the agent along with wetting and dispersing agents and sticking agents. For maximum chemical compatability those which are nonionic in character are preferred. Other nonionic or cationic surfactants are also satisfactory.

What is claimed is:

1. A compound of the formula:

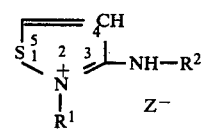

wherein $R^1$ and $R^2$ are the same and are, $C_1$ to $C_{16}$ alkyl, benzyl, or phenyl;

and $Z^-$ is a counter anion.

2. A compound according to claim 1 wherein $R^1$ and $R^2$ are isopropyl.

3. A compound according to claim 1 wherein $R^1$ and $R^2$ are n-propyl.

* * * * *